United States Patent [19]

Baughman

[11] Patent Number: 5,596,154
[45] Date of Patent: Jan. 21, 1997

[54] DILUTION CONTROL METHOD AND APPARATUS

[75] Inventor: Leonard Baughman, Indianapolis, Ind.

[73] Assignee: Enviroplan, Inc., Indianapolis, Ind.

[21] Appl. No.: 531,765

[22] Filed: Sep. 21, 1995

[51] Int. Cl.$^6$ ........................................... G01N 1/22
[52] U.S. Cl. .................. 73/863.01; 73/23.31; 73/863.03
[58] Field of Search .......................... 73/863.01, 863.02, 73/863.03, 23.28, 23.29, 23.31, 23.32, 23.33, 30.01, 30.02, 30.03, 30.04, 1 G

[56] References Cited

U.S. PATENT DOCUMENTS

| | | | |
|---|---|---|---|
| 3,699,814 | 10/1972 | Kaufman . | |
| 3,817,100 | 6/1974 | Anderson et al. | 73/213 |
| 4,008,601 | 2/1977 | Woods . | |
| 4,407,153 | 10/1983 | Furlong et al. | 628/201.24 X |
| 5,184,501 | 2/1993 | Lewis et al. | 73/23.31 |
| 5,487,312 | 1/1996 | Kahl et al. | 73/863.01 |

OTHER PUBLICATIONS

Jahnke, J. A., An Operator's Guide to Eliminating Bias in CEM Systems, EPA 430-R-94-016, Nov. 1994.
Source Technology Associates, Pressure and Temperature Effects in Dilution Extractive Continuous Emission Monitoring Systems, Electric Power Research Institute, TR-104700, Dec. 1994.
Appel, Dirk, Calibration of Dilution Extractive CEM Systems, Thermo Environmental Instruments, Inc., Jun. 17, 1994. 11 pages.
40 CFR, Part 75, App. A, Paragraph 3, and Part 75, App. B., Paragraphs 2.1.4 and 2.1.5 pp. 623 & 636.

*Primary Examiner*—Thomas P. Noland
*Attorney, Agent, or Firm*—Ice Miller Donadio & Ryan; Doreen J. Gridley

[57] ABSTRACT

An apparatus and method for maintaining a constant dilution ratio for a dilution probe used in a continuous emission monitoring system. The apparatus includes a regulator for regulating the flow of dilution gas to the probe, a mechanism for measuring changes in gas density of the emission gas and a mechanism for determining an adjusted flow rate for the dilution gas to the dilution probe based on the measured changes in gas density to control the dilution ratio. The method involves monitoring the gas density of the emission gas for a change in gas density. Upon the occurrence of a change in gas density, an adjusted flow rate of the dilution gas as required to control the dilution ratio is determined, and then the flow of dilution gas to the probe is adjusted to the adjusted flow rate. The use of the apparatus and method of the present invention provides a system capable of compensating for changes in gas density that does not require frequent calibration, is independent of the type of gas analyzer or gas constituent detection method used, and is able to be economically retrofitted into existing systems.

12 Claims, 8 Drawing Sheets

PRIOR ART

PRIOR ART

DILUTION CONTROL METHOD AND APPARATUS

FIELD OF THE INVENTION

This invention relates to continuous emission monitoring systems, and, in particular, to a system including a dilution probe in which corrections are made for changes in gas density.

BACKGROUND OF THE INVENTION

Emission standards for sulfur dioxide and nitrogen oxides were established with Title IV of the Clean Air Act Amendments of 1990. To meet these standards, continuous emission monitoring (CEM) systems were required to monitor these gases as well as carbon dioxide or oxygen, diluent gases, flue gas velocity, and opacity.

For all CEM systems, the measured results may be biased, i.e., inaccurate, due to a number of factors. Some of these factors relate to limitations or inherent problems in the equipment used in the system, while other factors are caused by changes in the stack which therefore result in changes in the extracted sample that are not compensated for by the system's components. Many of the factors contributing to bias for various types of CEM systems are discussed in "An Operator's Guide to Eliminating Bias in CEM Systems", United States Environmental Protection Agency, EPA 430-R-94-016.

A typical dilution extractive CEM system comprises a dilution probe within the stack, a gas conditioning system, a gas analyzer located proximate the stack, and a remote computer. Generally, stack (emission) gas is extracted from the stack through a sonic orifice in the dilution probe. Then clean gas (dilution air) is injected into the probe and mixed with the sample emission gas to produce a diluted sample which is then analyzed by the analyzer. Further analysis of the sample is achieved at the remote computer.

Extractive CEM systems using a dilution probe are often employed when a need exists to filter particulate matter that may be in the stack. Generally, when dilution probes are used, only the gas from the source enters the probe and the particulate matter does not enter the probe. Further, such systems draw gas from the stack at a rate significantly less than the source.

Dilution extractive CEM systems are generally application dependent, but yet had been proven to meet various applicable standards, such as linearity, calibration drift, and accuracy. Therefore, these CEM systems gained wide recognition as the system of choice. Recently, however, Environmental Protection Agency (EPA) standards have been promulgated which are more stringent than those of 1990. These new regulations caused problems with CEM systems in meeting the required accuracy.

To remain within the EPA requirements, many current CEM systems must generally be calibrated daily or every few days. Frequent calibration is not only costly, but it causes the user to lose valuable data, as data cannot be collected during the calibration process. Therefore, it is desirable to develop a dilution extractive CEM system which meets the new EPA requirements and does not require that the system be frequently calibrated.

One of the components having the largest impact on the accuracy of a dilution extractive CEM system is the dilution probe, such as the EPM Probe Heater Assembly Models 797.560/561 manufactured by EPM B. V. of Dalerstraat, Netherlands, and distributed in the United States by EPM Environment, Inc. of Mt. Prospect, Ill. The critical flow orifice extracts the gas at sonic velocity. The sonic velocity of the gas varies directly proportional to the square root of the density of the gas being analyzed. Generally, by calculating the change in density, it can be determined how much the dilution ratio has changed, and the appropriate adjustments can be made to achieve a correct reading.

In general, the problems associated with the dilution probe that result in bias are changes in: (1) absolute stack pressure; (2) stack temperature; (3) gas density; and (4) water droplet evaporation. Absolute stack pressure is the sum of the barometric pressure and the stack static pressure. Therefore, changes in absolute stack pressure result from changes in plant operating condition or from changes in weather conditions (barometric pressure). With regard to temperature, cessation of operation of the source will result in a large temperature change. The effects of temperature and pressure was studied by the Electric Power Research Institute. "Pressure and Temperature Effects in Dilution Extractive Continuous Emission Monitory Systems", Electric Research Institute, EPRI TR-104700, December, 1994.

To compensate for the non-linear changes resulting from changes in temperature, a heater is often placed around the dilution probe to maintain the probe at a constant temperature. Even if such corrective action is taken, corrections are still needed for the linear effect of change in absolute pressure. Generally, changes in pressure have been accommodated by correcting the collecting data according to the known linear relationship with the remote data acquisition system.

It is possible for corrections to be made for the effects of gas pressure (absolute pressure) and temperature on the gas density and gas analysis in a dilution extractive CEM system by calculating the effects and making appropriate adjustments. As previously stated, one way these adjustments are currently made is to correct the measured value after the analyzer has made its reading, i.e., to correct the value with the remote data acquisition system.

There are several problems associated with correcting the value at a remote computer. Latent correction means that any display of data collected near the probe is incorrect—the correct values can only be seen at the remote computer, not at the analyzer. Because calibration of the system occurs away from the remote computer, a display must be located near the analyzer, and that display must necessarily be connected to the remote computer. It is therefore desirable to provide a CEM system which corrects for changes in gas density, including changes in absolute stack pressure and stack temperature, without requiting that the corrections be made a remote computer sight.

It is also desirable to provide a system for correcting for changes in gas density that may be used with different types of analyzers as different detection methods may be used. Such universality of application permits use of the corrections on existing CEM systems as well as future CEM systems.

One of the advantages of correcting the collected data with the data acquisition system is the fact that the capability to correct the data may easily be added into an existing system. The "retrofitability" stems from the fact that computer software is added to the already existing data acquisition system to correct for changes gas density. Therefore, it is desirable for any other method and apparatus provided to correct for changes in gas density to also be able to be retrofitted into existing systems. Such a retrofit should be cost-conscious, not only as to the purchase and maintenance costs of any additional or modified equipment that may be necessary, but also with regard to the costs associated with installation of the retrofit.

OBJECTS OF THE INVENTION

Accordingly, one object of the present invention is to provide a method and apparatus for continuous emission monitoring using a dilution probe that is able to compensate for changes in the dilution ratio caused by changes in stack and atmospheric pressures, gas density and stack temperature.

Another object of the present invention is to provide a method and apparatus for continuous emission monitoring which does not require that the system be frequently calibrated so that valuable time and data are not lost due to frequent calibrations.

Yet another object of the present invention is to provide a method and apparatus for continuous emission monitoring which compensates for changes in gas density at the dilution probe rather than at a remote computer sight.

Another object of the present invention is to provide a correction system which compensates for changes in gas density independent of the type of analyzer/detection method used in the CEM system.

Still another object of the present invention is to provide a method and apparatus for continuous emission monitoring which corrects for changes in gas density, absolute stack pressure and stack temperature, and is able to be economically retrofitted into existing CEM systems.

SUMMARY OF THE INVENTION

Figure 1:
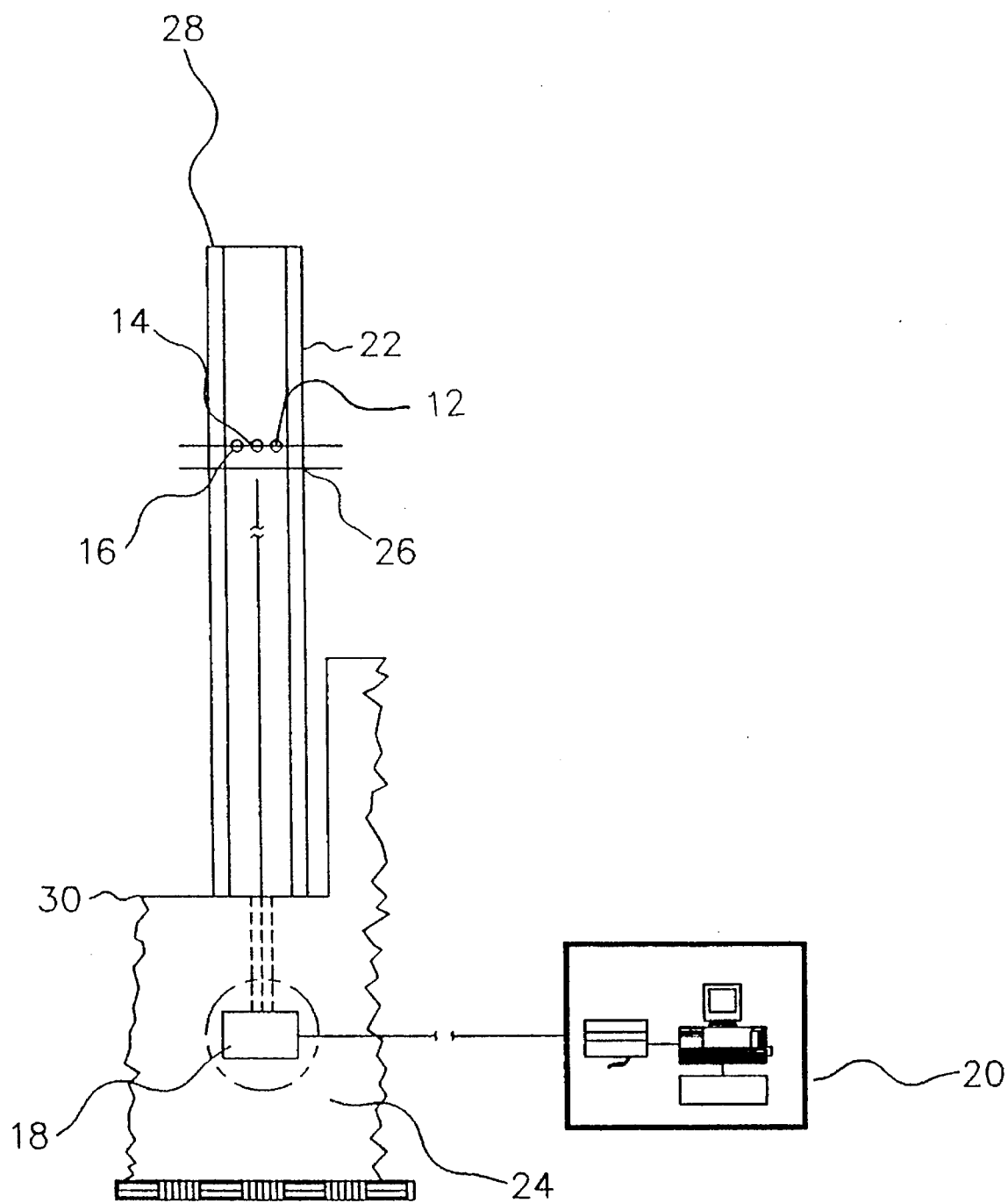
FIG. 1 shows a diagrammatic view of one embodiment of the continuous emission monitoring system of the present invention.

The present invention provides a method and apparatus for controlling the dilution ratio as measured at a dilution probe used in a continuous emission monitoring system. Such a CEM system usually includes a dilution probe for the collection of a sample of emission gas emitted from a source located at the bottom of a hollow stack, combining the sample emission gas with a dilution gas, and yielding a diluted sample gas. The constituents of the diluted sample gas are analyzed by a gas analyzer, and the analyzer is connected to a remote data acquisition system for further analysis of the diluted sample gas.

The control apparatus of the present invention includes a regulator for regulating the flow of dilution gas to the probe. The regulator is disposed between the dilution gas source and the probe. The apparatus also includes a means for measuring changes in gas density of the emission gas, and a means for determining an adjusted flow of the dilution gas based on the measured changes in gas density to control the dilution ratio. The determining means is therefore connected to both the regulator and the measuring means.

The control apparatus of the present invention may be easily and economically retrofitted into existing CEM systems. Changes in stack pressure, atmospheric pressure, stack temperature, and other factors affecting gas density are capable of being accounted for by the control apparatus. The apparatus will provide good, actual readings at the gas analyzer, thus eliminating the need to correct the data at the data acquisition system. Further, the apparatus may be used in connection with any gas analyzer and is independent of the gas detection method used in the system. Also, use of the control apparatus reduces the frequency with which the system must be calibrated since a relatively constant dilution ratio is maintained during operation of the CEM system.

The method of the present invention involves the step of monitoring the gas density of the emission gas for a change in the gas density. Upon the occurrence of a change in gas density, an adjusted flow value for dilution gas provided to the probe is determined based on the change in gas density in order to control the dilution ratio. Then, the flow of dilution gas to the probe is adjusted to the determined adjusted flow value. In one embodiment, "gas density" is measured in terms of changes in stack pressure and changes in atmospheric pressure.

This method is advantageous in eliminating the requirement that values read by the analyzer must be corrected, as by a remote data acquisition system, for example. Rather, the values at the analyzer will be accurate. Also, the system requires less frequent calibration since a relatively constant dilution ratio is maintained. The steps of the method of the present invention are not numerous nor complex, and therefore, relatively inexpensive equipment may be employed to perform the above steps. Further, the method is not time consuming to perform, thereby resulting in quick, real time correction for changes in gas density of the emission gas.

DETAILED DESCRIPTION

Referring now to the drawings, and in particular to FIG. 1, there is shown a diagrammatic view of one embodiment of the continuous emission monitoring system of the present invention. The CEM system of FIG. 1 comprises a dilution extraction CEM system which includes dilution probe 12, opacity reflector assembly 14, opacity transceiver assembly 16, shelter 18, data acquisition system 20, and associated cabling (for both electrical and gas connections as described in further detail herein). The CEM system of FIG. 1 is positioned to measure emissions from stack 22 connected to building 24 inside which is the source of the emission gases which escape through stack 22.

Dilution probe 12, opacity reflector assembly 14, opacity transceiver assembly 16 are located at port level 26 of stack 22 near top 28 of stack 22. Shelter 18 is positioned inside building 24 below bottom 30 of stack 22. Data acquisition system 20 is separated from shelter 18 and is usually remotely located from shelter 18 in a separate control room and may be connected by RS-485 cabling, for example, to shelter 18. Shelter 18 contains various circuitry and gas supplies (see FIG. 4) for analyzing gases detected by opacity reflector assembly 14, opacity transceiver assembly 16, and dilution probe 12 as is known in the art. Data acquisition system 20 provides further analysis of the data collected and analyzed, and also provides an operator with control over the operation of the CEM system of FIG. 1.

Figure 2:
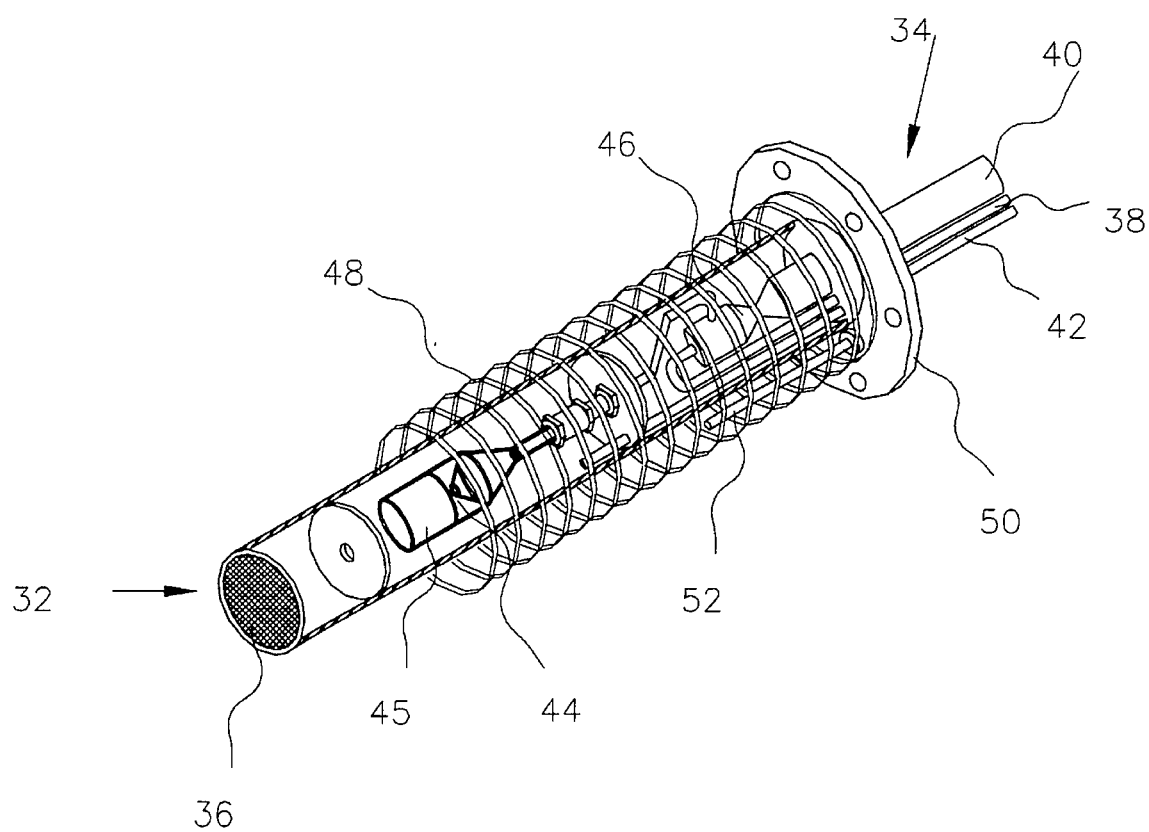
FIG. 2 shows a partial cross-sectional view of a prior art dilution probe used in the system of the present invention.

FIG. 2 shows a cross-sectional view of a prior art dilution probe as is used in the system of the present invention. The dilution probe illustrated in FIG. 2 is the EPM Probe Heater Assembly Models 797.560/561 manufactured by EPM B. V. of Dalerstraat, Netherlands, and distributed in the United States by EPM Environment, Inc. of Mt. Prospect, Ill. Dilution probe 12 has first and second opposing ends 32 and 34. First end 32 of dilution probe 12 is that which is inserted into stack 22 to collect samples of gas emissions from within hollow stack 22. Located at first end 32 is screen 36 into which the emitted (sample) gas passes. At second end 34 of dilution probe 12 are three gas lines—dilution gas line 38 into which dilution gas, such as compressed air, enters dilution probe 12; diluted sample gas line 40 though which the combination of the sample gas and the dilution gas passes to shelter 18; and calibration gas line 42 through which calibration gases enter dilution probe 12.

Dilution probe 12 also includes sonic orifice 44 through which sample gas passes, and venturi 46 in which sample gas is combined with dilution gas to exit through diluted sample gas line 40 for subsequent analysis. Venturi 46 is also an ejector pump used to maintain the flow of sample gas through orifice 44 to be at sonic velocity. Positioned between screen 36 and sonic orifice 44 is quartz wool filter 45, for filtering particulate matter from the sample gas. The general operation of dilution probe 12 is discussed herein in association with FIG. 3.

In the embodiment of FIG. 2, dilution probe 12 also includes heater 48 about that portion of dilution probe 12 from sonic orifice 44 to mounting flange 50 used to mount dilution probe 12 to stack 22. Heater 48 is employed to maintain dilution probe 12 at a constant temperature to compensate for the non-linear changes in gas density resulting from changes in sample gas temperature. To regulate the temperature of heater 48, dilution probe 12 also includes thermocouple 52.

Figure 3:
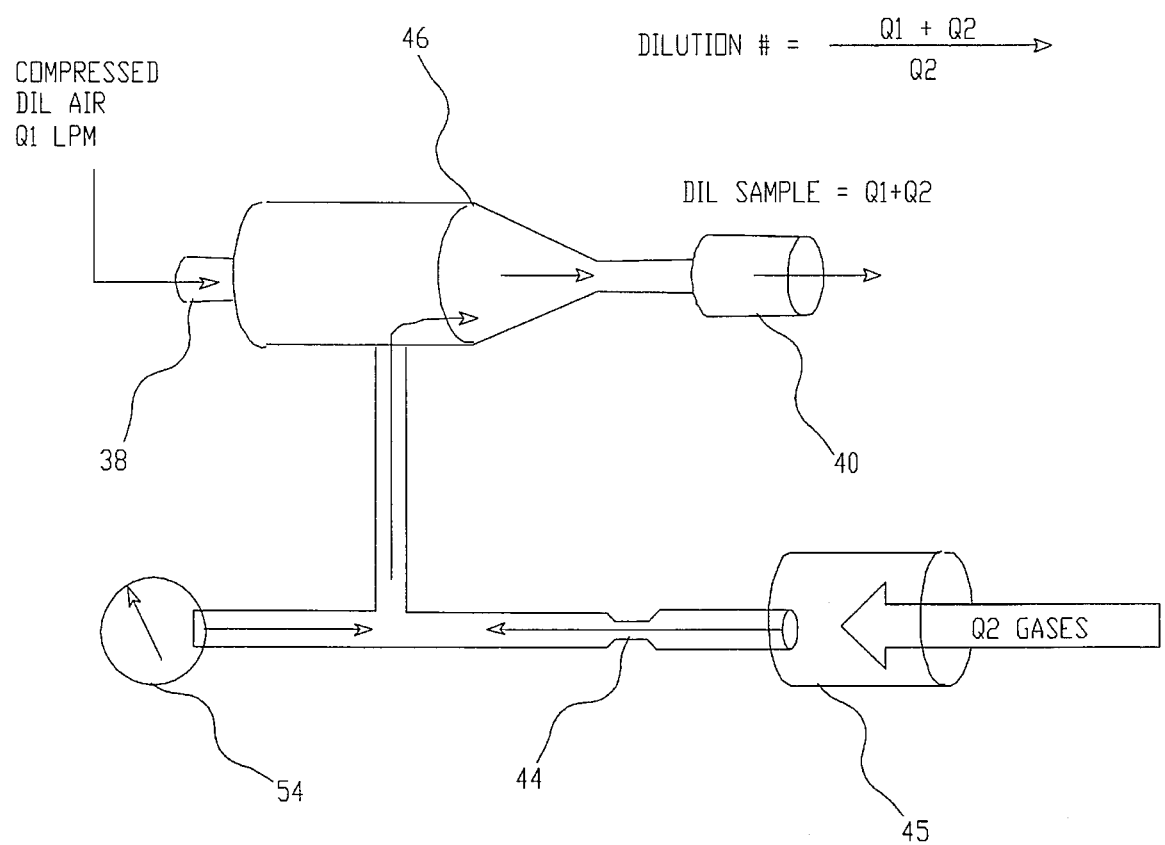
FIG. 3 shows a simplified diagram of the operation of a prior art dilution probe as is used in the system of the present invention.

Referring now to FIG. 3, there is shown a diagrammatic view of the prior art dilution probe used in connection with the CEM system of the present invention. Sample (stack) gas is continuously extracted through filter 45 and critical orifice 44 by ejector pump 46 mounted inside probe 12. The main dilution air stream creates a pressure differential in ejector pump 46 which is used to extract stack gas from stack 22 through orifice 44. Stack gas is mixed with dilution gas from dilution gas line 38 and exits probe 12 through diluted sample gas line 40 as diluted sample gas.

The dilution number (ratio) is equal to the sum of dilution gas (Q1) plus sample gas (Q2) divided by sample gas (Q2). The value of dilution gas Q1 can be adjusted by varying the flow (flow rate or pressure) of the dilution gas to probe 12. Stack gas Q2 is defined by orifice 44 and the pressure in stack 22. The flow of stack gas will be reached when the pressure differential (measured by vacuum gauge 54) in ejector pump 46 ranges from 15 to 24 inches of mercury.

The diluted sample gas (Q1+Q2) is transported by diluted sample gas line 40 to gas analyzers (see FIG. 4) held in shelter 18 for detection of the types of gases contained in the diluted sample gas. The active dilution control panel (discussed herein in association with FIGS. 4 and 5) is used in the present invention to set and monitor the pressure and vacuum at probe 12. The active dilution control panel also monitors the flow of calibration and purge gases to probe 12.

Figure 4:
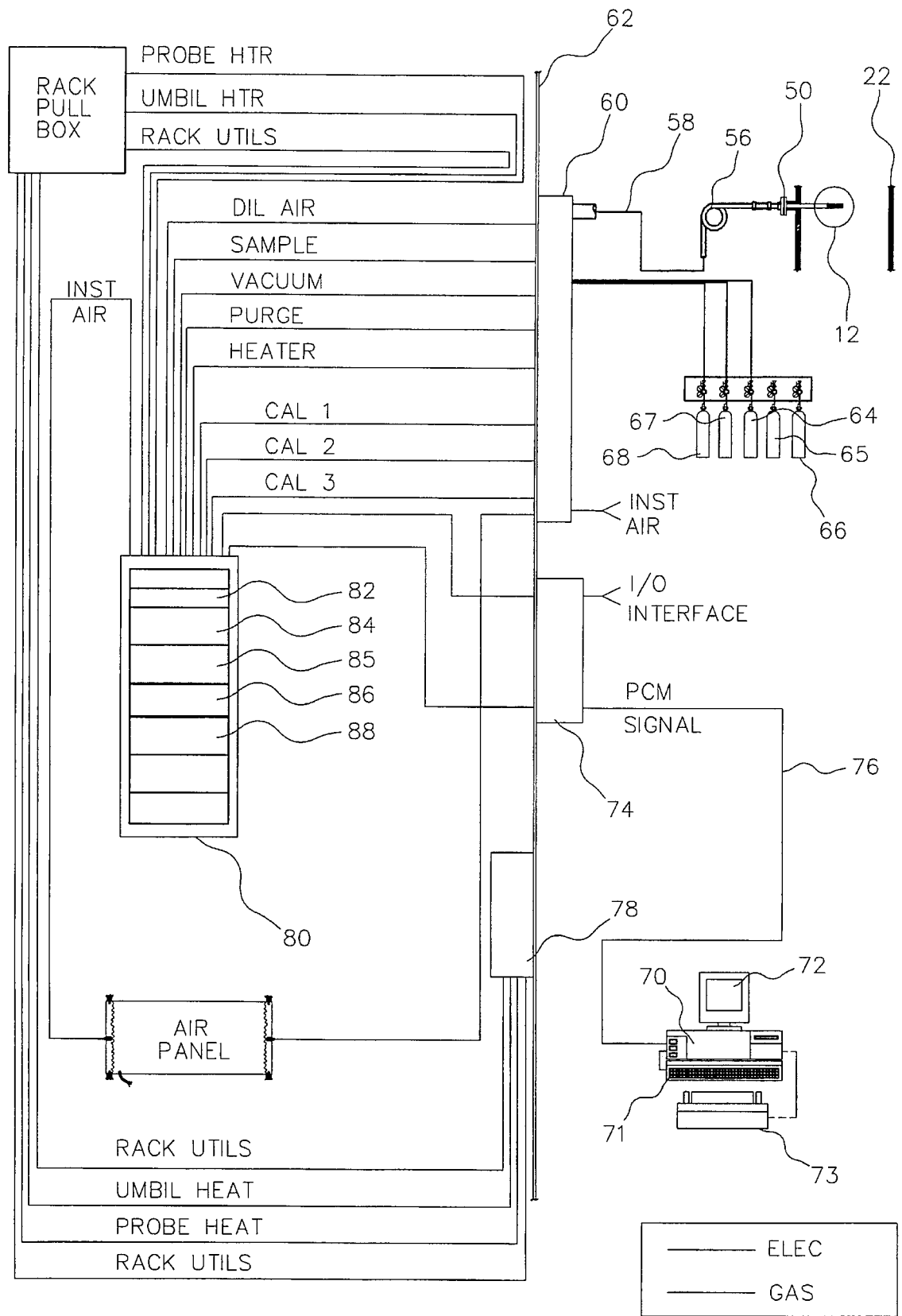
FIG. 4 shows a block diagram of one embodiment of the continuous emission monitoring system of the present invention.

Referring now to FIG. 4, there is shown a block diagram of one embodiment of the continuous emission monitoring system according to the present invention. In this diagram, the dashed lines represent electrical connections and the solid lines represent gas or air line connections. Dilution probe 12 is connected to stack 22 by flange 50. Connected to probe 12 is service loop 56 for providing a means to remove probe 12 for service thereof. Stack umbilical 58 extends through service loop 56 to probe 12 to connect probe 12 to umbilical breakout box 60 attached to shelter wall 62 of shelter 18. Stack umbilical 58 contains the electric and air lines for handling calibration gases, dilution gas, probe heating, and return of diluted sample gas.

Also connected to umbilical breakout box 60 are three lines servicing gases housed in gas cylinders 64–68. In this embodiment, first gas cylinder 64 contains low linearity calibration gas, second cylinder 65 contains high linearity calibration gas, third gas cylinder 66 contains zero air, fourth gas cylinder 67 contains mid-linearity calibration gas, and fifth gas cylinder 68 contains high daily calibration gases. Gases housed in gas cylinders 64–68 are used for calibration purposes in a manner that is well known in the art. Such calibration gases are brought through calibration gas line 42 into probe 12 so that the system may be calibrated as to both gas analysis and gas density. Similarly, any gas within probe 12 may be purged through calibration gas line 42, such as is done prior to calibration to ensure that only calibration gases reside within probe 12 for calibration purposes.

In this embodiment, data acquisition system 20 includes a personal computer connected to a printer. Specifically, data acquisition system 20 includes central processing unit 70, keyboard 71, display terminal 72 and printer 73 connected to central processing unit 70. Central processing unit 70 is connected to signal breakout box 74 which is attached to shelter wall 62 of shelter 18 by data communications line 76. Data communications line 76 carries signals for operator communication with the remainder of the CEM system shown in FIG. 1.

Also connected to shelter wall 62 is power panel 78 for the provision of electrical power to electrical rack 80, heat provided to stack umbilical 58, heat provided to probe 12, and rack 80 utilities. In this embodiment rack 80 is a 19-inch electrical rack containing probe heater controller 82, active dilution control panel 84, system controller 85, nitrous oxide analyzer 86 and carbon dioxide analyzer 88. Analyzers 86 and 88 use various methods to determine the nitrous oxide and carbon dioxide content of diluted sample gas collected by probe 12 as is well known in the art. Probe heater controller 82 controls the temperature of heater 48 of probe 12 as is well known in the art. The purpose and operation of active dilution control panel 84 is described in further detail herein in association with FIG. 5. System controller 85 controls the functions of the CEM system shown in FIG. 1, including calibration of the CEM system shown in FIG. 1, sampling of stack gas with probe 12, and analysis of the stack gas with analyzers 86 and 88.

Figure 5:
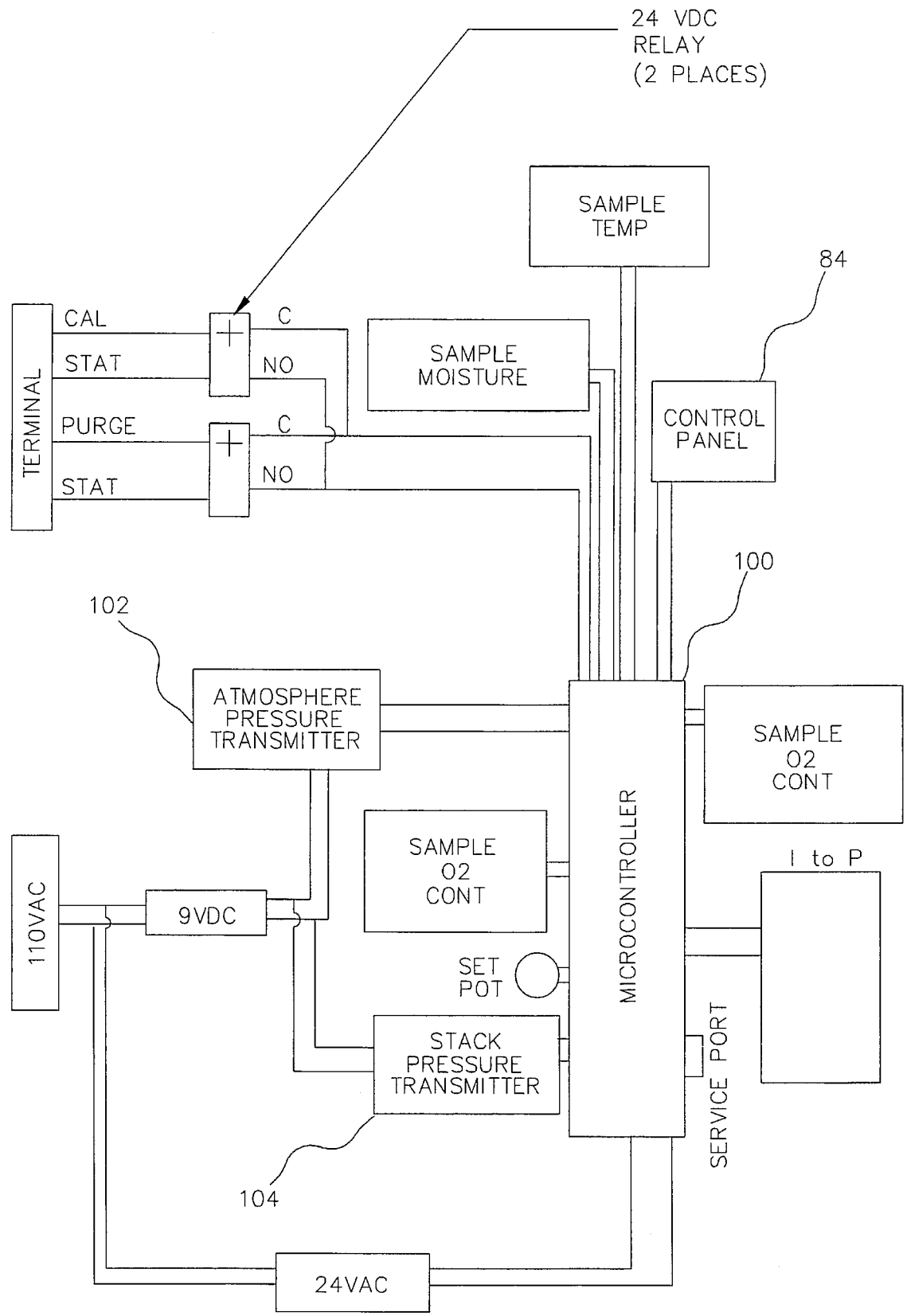
FIG. 5 shows a block diagram of the active dilution control panel of the present invention.

FIG. 5 shows a block diagram of the active dilution control panel of the present invention. The control and calculation functions of active dilution control panel 84 are accomplished by micro-controller 100, which, in this embodiment comprises a Model TCX 870 Controller manufactured by Andover Controls. Input to micro-controller 100 are values of the atmospheric pressure and stack pressure. Atmospheric pressure is determined by atmospheric pressure transmitter 102 which detects the atmospheric pressure through a vent (not shown) in rack 80. Stack pressure is determined by stack pressure transmitter 104 which receives a pressure reading through calibration gas line 42. Thus, to read stack pressure, calibration gas cannot be entering probe 12 or a false reading, a reading corresponding to the pressure of the calibration gas, will be read by stack pressure transmitter 104. Also, probe 12 should not be in the process of being purged when reading stack pressure. Therefore, micro-controller 100 receives calibration status and purge status information from system controller 85 through the bus of rack 80.

In the embodiment of FIG. 5, other inputs are illustrated as being provided to micro-controller 100. Specifically, a reading of sample carbon dioxide content, sample moisture content, sample temperature, dilution air temperature, and sample oxygen content may also be provided to micro-controller 100. Various appropriate mechanisms, such as analyzers or thermometers, may be used to collect such data and the specific mechanisms are not essential to the operation of dilution control method and apparatus of the present invention.

Considering now the specific control functions of active dilution control panel 84, several facts are relevant, including:

1. The velocity of gas passing through orifice 44 of probe 12 is proportional to the square root of the density of the stack gas.
2. The density of a gas is proportional to the absolute pressure of that gas (Pv=nRT).
3. The density of a gas is inversely proportional to the absolute temperature of that gas (Pv=nRT).
4. The molecular weight of a gas mixture, such as the diluted sample gas, is equal to the sum of the volume percentages of the gases (stack gas and its constituent gases and dilution gas) times their molecular weights.
5. The density of a gas is proportional to the molar weight.
6. The dilution ratio for a mixture of stack gas and dilution gas is equal to the volume of the sample gas divided by the total volume of the mixture provided that both gases are at the same temperature and pressure.

Figure 8:
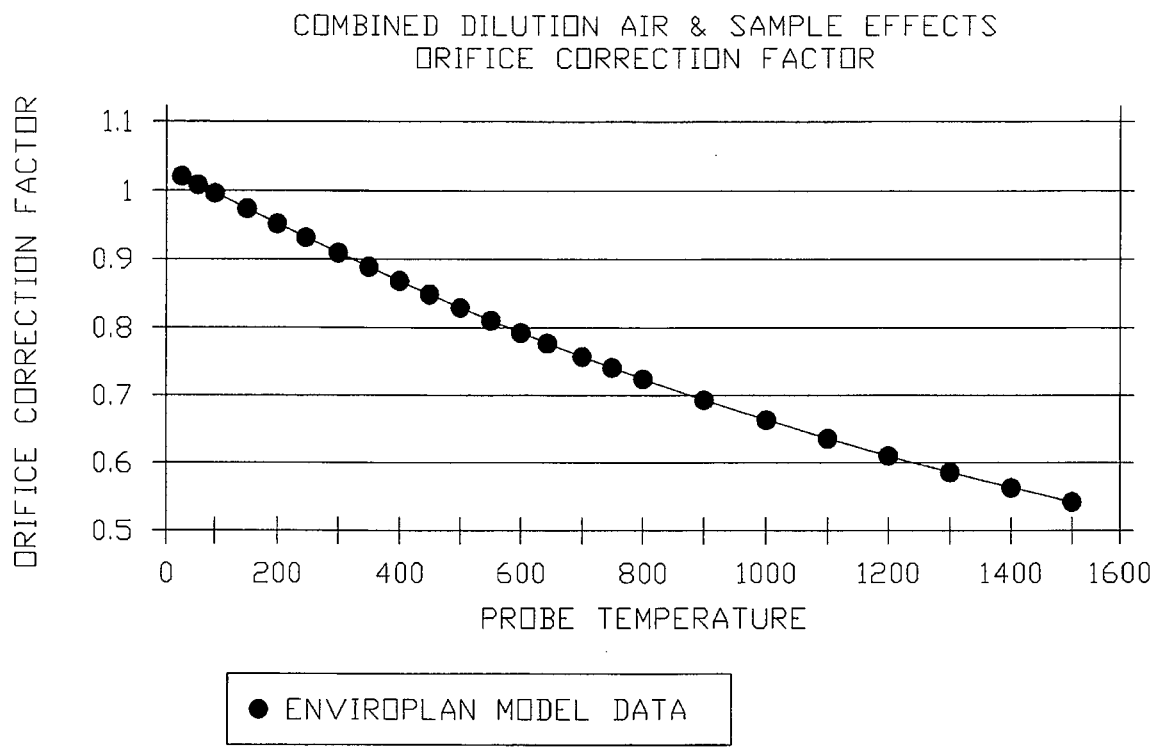
FIG. 8 shows a graph of the orifice correction factor.

The change in volume of the stack gas passing through orifice 44 can be approximated by multiplying the original flow rate by one-half the square root of the ratio of the original gas density by the final gas density, or $$Q2 = Q1 * (D1/D2)^{0.5}$$

where D1 is the density of the original gas and D2 is the density of the final gas. The relationship of the orifice correction factor the probe temperature as determined experimentally for the present system is shown in FIG. 8.

Figure 9:
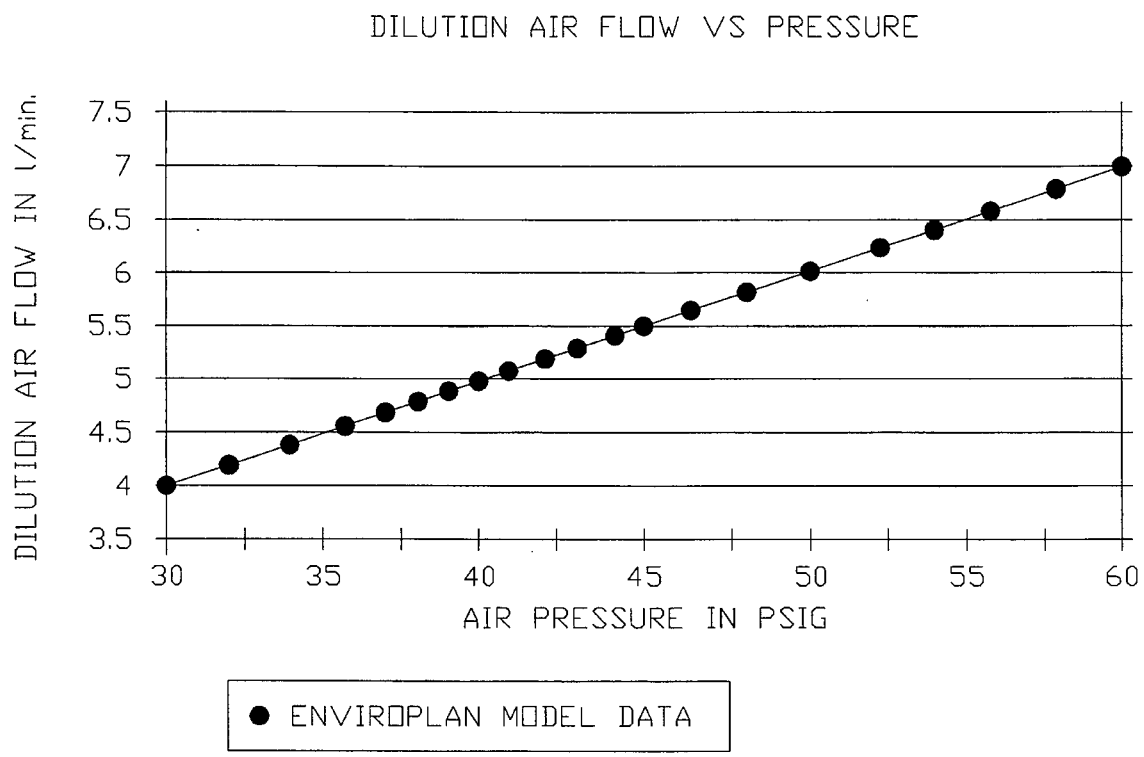
FIG. 9 shows a graph of the dilution air flow versus the air pressure.

For the present invention in which an EPM probe is used and wherein the system is vented to the atmosphere at the analyzer location (rack 80), the dilution air flow is proportional to the supply pressure to the probe. This relationship was experimentally determined to be:

$$Q = 0.103 * P + 0.88$$

where Q is the dilution air flow in liters per minute, and P is the pressure in psig. This relationship is illustrated in FIG. 9 as determined experimentally by the Applicant.

Figure 6A:
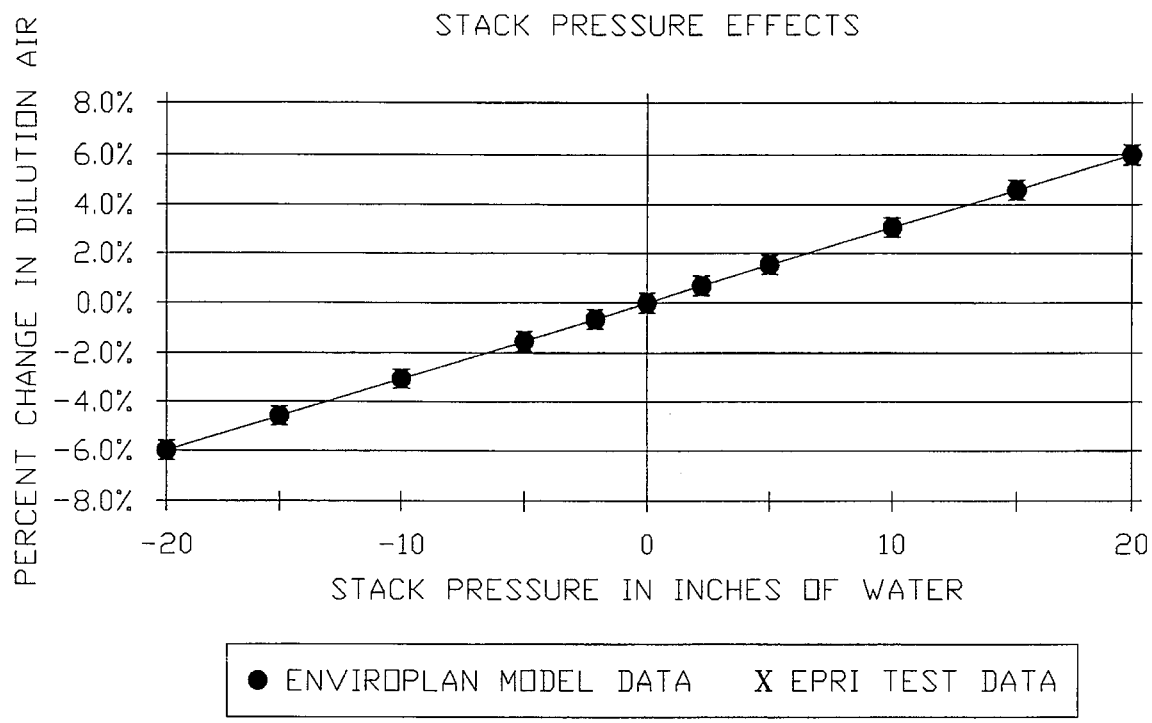
FIG. 6A shows a graph of the effects of changes in stack pressure on the dilution number.
Figure 6B:
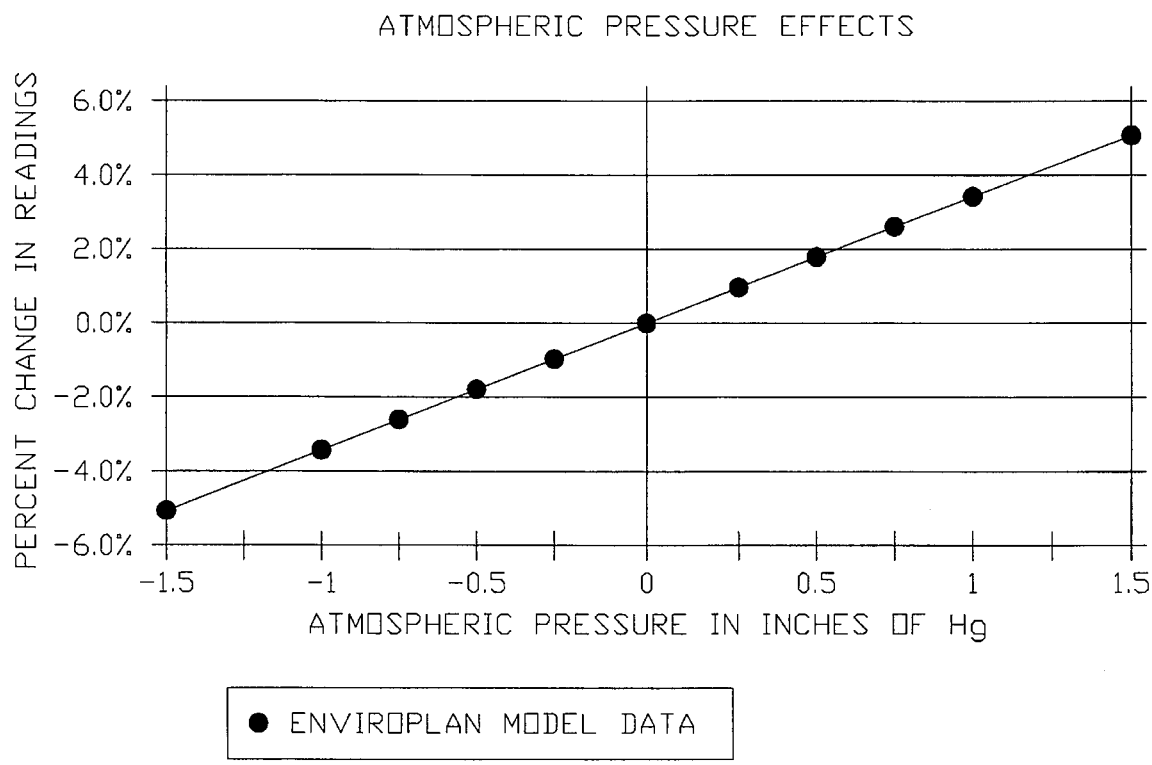
FIG. 6B shows a graph of the effects of changes in atmospheric pressure on the dilution number.

With regard to the effects of stack pressure and atmospheric pressure on dilution number, FIGS. 6A and 6B illustrate these effects as calculated using the above relationships for the present system and as determined experimentally by the Applicant. Note that both effects are substantially linear. The relationships may be summarized as follows:

1) The change in stack pressure required to cause a 1% change in dilution ratio is approximately 3.45 inches of water column.
2) The change in atmospheric pressure required to cause a 1% change in dilution ratio is approximately 0.3 inches of mercury. This same 0.3 inch change of mercury will cause the number of gas molecules present in the measurement cell of the analyzer to change 1%. This means that to compensate for both effects, the probe effect and the analyzer effect, the dilution ratio must change by 2% for every 0.3 inch of mercury change in atmospheric pressure.
3) Based upon the flow relationship for the probe, a 1 psig change in pressure to the probe will change the dilution ratio by 2%.

The above relationships control the dilution ratio by varying the pressure to probe 12 through the use of micro-controller 100 and current-to-pressure transducer (see I to P on FIG. 5). The I to P transducer is disposed between the source of dilution gas and probe 12, and controls the air pressure to dilution probe 12. Further, control is accomplished according to the above relationships in an open loop control scheme, such as the program of the Appendix which executes on micro-controller 100.

Active dilution control panel 84 of the present invention controls the air pressures to ejector pump 46 in response to changes in gas density. Although the flow of air to ejector pump 46 could be monitored and controlled by active dilution control panel 84, the embodiment discussed herein controls air pressure. The election to monitor and control pressure was made to limit the expense of the system; however, control and monitoring of the flow of dilution air is within the scope of the invention.

It should be recognized that changes in absolute stack pressure (stack static pressure and barometric pressure) not only effects the sample flow through the probe, but also effects the analyzer's readings by changing the number of molecules in the analyzer's sample chamber. By varying dilution ratio in accordance to changes in absolute stack pressure, the present invention ensures that the number of molecules in the sample chamber of the analyzer remains controlled and relatively constant as the absolute stack pressure changes. Thus, the analyzer's readings are not effected by the changes in absolute stack pressure. The readings of the analyzer have been corrected when the dilution control system of the present invention is employed, thereby resulting in real time control of the dilution ratio.

It will be appreciated by those of skill in the art that the active dilution control subsystem of the present invention is advantageous over the prior art method of correcting the collected data values at the data acquisition system. Because corrections are made in the shelter electronics before the analyzer, any values read, whether at the shelter (analyzer) or at the remote data acquisition system, are accurate. Thus, there is no need to provide access to a remote data acquisition system at or near the analyzer when calibrating the analyzer. This method has further advantage because the corrections are independent of the type of analyzer or the detection method used in the system.

It will also be appreciated that the particular type of probe used in the CEM system of the present invention will impact the adjustments made by the system. The relationships for the flow changes should be experimentally determined for that probe. It will be appreciated, however, that the effects of atmospheric pressure and stack pressure will be the same for any probe utilizing a critical flow orifice. Therefore, the only modification required to the above method is the use of difference scaling values.

It will be further appreciated that the dilution control subsystem of the present invention may be easily and economically retrofitted into an existing system. Specifically, active dilution control panel 84 is inserted into an available slot in rack 80. Because active dilution control panel 84 contains internally mounted pressure transducers 102 and 104, the existing dilution air supply line and the existing pressure regulator may be removed or disabled. Stack pressure transceiver 104 must then be connected to the calibration gas line of the system, and a signal provided to active dilution control panel 84 to notify active dilution control panel 84 when either a calibration or purge of the probe is in progress so active dilution control panel 84 does not cause stack pressure to be measured during the calibration or purging process. If the dilution control subsystem of the present invention were to compensate for changes in gas analysis as discussed later herein, active dilution control panel 84, and in particular micro-controller 100, would need to be connected to the analyzers contained in rack 80.

It will also be appreciated by those of skill in the art that in CEM systems which utilize a dilution probe which does not contain a heater to keep the temperature of the gases constant, gas density of the diluted sample gas will be effected by temperature changes. One must consider the change in dilution air density, the change in sample gas density, the sonic velocity change of the sample gas, and the viscosity effect for both the sample gas and the dilution gas.

Figure 7A:
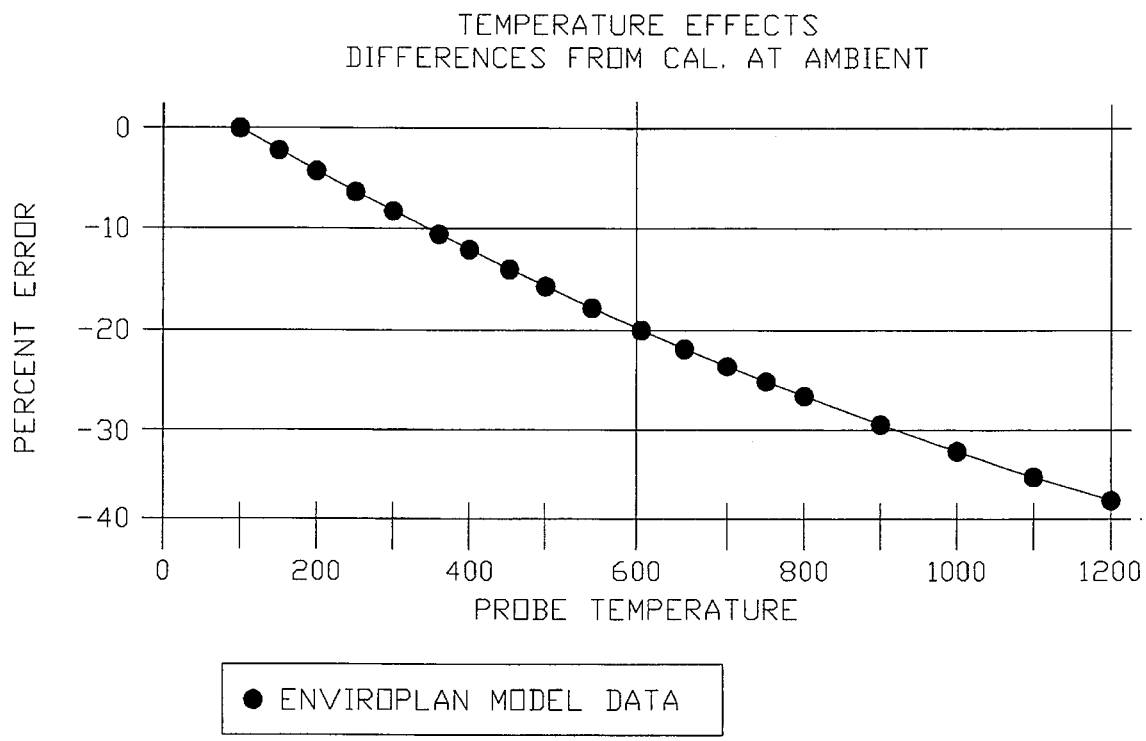
FIG. 7A shows a graph of the effects of temperature effects on the diluted sample.
Figure 7B:
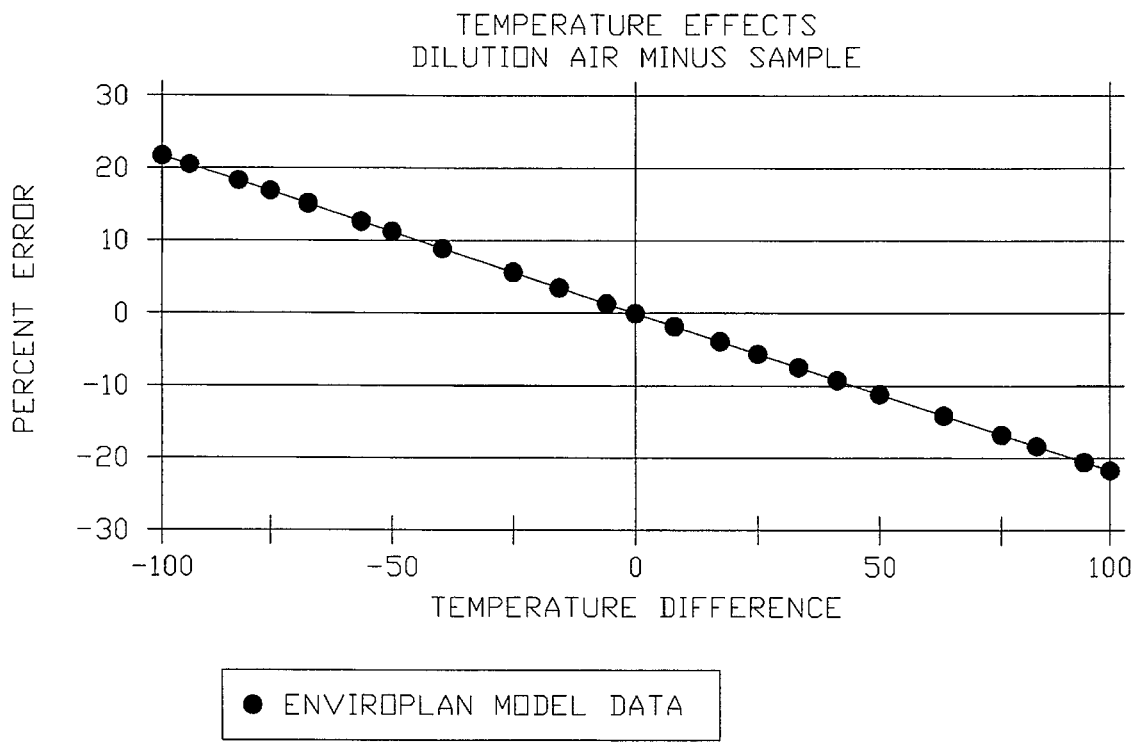
FIG. 7B shows a graph of the effects of temperature effects for the dilution air minus the sample.

It is possible to experimentally determine these effects to change the pressure of the dilution air as discussed above in association with stack temperature and atmospheric temperature. However, because this relationship is non-linear and very complex to calculate, it may be preferable to control the temperature of the dilution and sample gases by use of heaters as is done in the present invention. Illustrations of the effects of temperature for the present invention, as experimentally determined, are found in FIGS. 7A and 7B.

It will also be appreciated that the approach used for stack and atmospheric temperature changes can be implemented to considered changes in the sample gas constituents (sample analysis). According to Dr. Dirk Appel ("Calibration of Dilution Extractive CEM Systems", Thermo Environmental Instruments, Inc., June 17, 1994), the sonic velocity effect is calculated using the equation:

$$FGCF = 1.0025 + 0.0028(CO2)\% - 0.0020(H2O)\% + 0.0007(O2)\%$$

where FGCF is the Flue Gas Correction Factor. The true emission is equal to the measured emission times FGCF. For use in the above-described method, if successive FGCF's are determined, $FGCF_1$ and $FGCF_2$, the ratio of $FGCF_2/FGCF_1$ is proportional to the change in dilution number caused by the sonic velocity change. To correct for the viscosity effect, the adjusted value is $0.5*(FGCF_2/FGCF_1)$ in magnitude, and in the opposite direction from the sonic velocity effect. Thus, the net effect is $0.5*(FGCF_2/FGCF_1)$.

As used herein and in the claims, the term "changes in gas density" refers to changes in absolute stack pressure, stack temperature, and/or gas constituents. Also, it will be appreciated that the above embodiments are merely illustrative and that those of ordinary skill in the art may readily envision or develop similar embodiments within the scope of the present invention.

APPENDIX

PROGRAM FOR ACTIVE DILUTION CONTROL PANEL

'Date :Sept 12, 1995   10:20:24
'User : INFINITY1   ACC

Dictionary : INFINITY1 : 1

| 'TYPE | : NAME | : HANDLE | : PORT | :SERIALNUM | : INFINETID |
|---|---|---|---|---|---|
| infinetctlr | : DCP | : 7002 | : 1 | : 196697 | : 2 |

EndDictionary

Dictioanary : INFINITY1   DCP

| 'TYPE | : NAME | : HANDLE |
|---|---|---|
| Input | : INP.Atm | : 2 |
| Input | : INP.CalPurge | : 4 |
| Input | : INP.Pot | : 1 |
| Input | : INP.Stack | : 3 |
| Output | : OUT.Dilute | : 6 |
| Numeric | : AtmRamp | : 9 |
| Numeric | : StackRamp | :10 |
| Program | :DILUTION | : 5 |
| Program | :Transfer | : 11 |

EndDictionary

BeginController : INFINITY 1 DCP

Object : INP.Atm
 Type : Input
 LastChange 1-7-1989   11:34:35 pm
 Channel : 2
 Electype : Voltage
 Units : Psi
 EngScaleTop : 32
 ElecScaleTop : 3.1
 ElecScaleBot : .5
 Size : 288
 LogType : LogInstantaneous
 LogInterval : 0 00:05:00
 LCDState : Disabled
EndObject Object : INP.CalPurge
Type : Input
LastChange : 1-7-1989   11:35:02 pm
Clhannel : 4
ElecType : Digital
Size : 288
LogType : LogInstantaneous
LogInterval : 0 00:05:00
LCDState : Disabled
EndObject Object : INP.Pot
Type : Input
LastChange : 1-7-1989   11:33:36 pm
Channel : 1
ElecType : Voltage
Units : Kohm
Size : 288
LogType : LogInstantaneous
Conversion : (1+ (3.2258 * (ElecValue - 0.47)) + (1.25162 * ( ElecValue  - 0.47) * (ElecValue -     1.71))
LogInterval : 0 00:05:00
LCDState : Disabled
EndObject Object : INP.Stack
Type : Input
LastChange : 1-7-1989   11:33:14 pm
Channel : 3
ElecType : Voltage
Units : Psi
EngScaleTop : 69.3
EngScaleBot :- 69.3
ElecScaleTop : 3
ElecScaleBot : .5
Size : 288
LogType : LogInstantaneous
LogInterval : 0 00:05:00
LCDState : Disabled
EndObject Object : Out.Dilute
 Type : Output
 LastChange : 1-7-1989  11:35:34 pm
 Channel : 4
 ElecType : Current
 Units : Psi
 EngScaleTop : 60
 EngScaleBot : 30
 ElecScaleTop : 20
 ElecScaleBot : 4
 Size : 288
 LogType : LogInstantaneous
 LogInterval : 0 00:05:00
 LCDState : Disabled
EndObject Object : AtmRamp
 Type : Numeric
 LastChange : 1-7-1989  11:31:25 pm
 Units : Psi
 Size : 60
 LogType : LogInstantaneous
 LogInterval : 0 00:00:01
 LCDState : Disabled
EndObject Object : StackRamp
 type : Numeric
 LastChange : 1-7-1989  11:31:13 pm
 Units : Psi
 Size : 60
 LogType : LogInstantaneous
 LogInterval : 0 00:00:01
 LCDState : Disabled
EndObject Object : Poweruptime
 Type : SystemVariable
 LastChange : 1-7-1989  11:37:34 pm
 Size : 365
 LogType : LogInstantaneous
 LogInterval : 1 00:00:00
 LCDState : Disabled
EndObject Object : DILUTION
Type : Program
Discription : Determines dilution output
LastChange : 1-7-1989  11:30:39 pm
Status : Active
AutoStart : True
FiringOrder : Transfer
Code :
    Numeric Pot, Atm, Stack, LastStack, D1, D2, D3, Dilute, FLAG Calcs:
    Set Pot to imp.pot / 10
    Set Atm to average (AtmRamp)
    If Atm is not between 16 and 32 then set Atm to 30
    If IMP.CalPurge is on then set FLAG to
    If IMP.CalPurge is off and FLAG = then
      Set FLAG to 0
      Goto Wait
    End If If Imp.CalPurge is off then
      Set stack to average (StackRamp)
      If Stack is above 40 or below -40 then set stack to lastStack else set lastStack to Stack
    End If Set D1 to 30 + Pot * 30
    Set D2 to D1 * (Atm / 29.92)
    Set D3 to D2 * (1 + Stack / 3.45 / 65)
    Set Dilute to D3
    Set out.Dilute to Dilute GoTo Calcs Wait:
    If TS >= 120 then GoTo Calcs

What is claimed is:

1. An apparatus for controlling the dilution ratio of a dilution probe connected to a source of emission gas and a source of dilution gas, the probe having a means for receiving sample emission gas, a means for receiving the dilution gas, and a means for emitting a diluted sample gas comprising a mixture of the sample emission gas and the dilution gas, the dilution ratio defined as the ratio of the flow of diluted sample gas from the probe to the flow of sample emission gas to the probe, the control apparatus comprising:

a regulator for regulating the flow of dilution gas to the probe, the regulator disposed between the dilution gas source and the probe;

means for measuring changes in gas density of the sample emission gas; and means for determining an adjusted flow value for the dilution gas provided to the probe, the adjusted flow value based on the measured changes in gas density and determined to control the dilution control ratio, the determining means connected to the regulator and the measuring means.

2. A continuous emission monitoring system for monitoring an emission gas in a hollow stack, the system comprising:

a source of dilution gas;

a dilution probe having first, second and third gas ports, the first port extending within the stack to collect sample emission gas therefrom, the second port operably connected to the dilution gas source, and the third port connected to the first and second ports and providing a diluted sample gas from the probe, the diluted sample gas comprising a mixture of the dilution gas and the sample emission gas;

means for regulating the flow of dilution gas to the probe, the regulating means disposed between the dilution gas source and the second port of the probe;

means for measuring changes in gas density of the sample emission gas; and means for determining an adjusted dilution gas flow value based on the effect of measured changes in gas density to control the dilution ratio, the dilution ratio defined as the ratio of flow of diluted sample gas from the probe to flow of sample emission gas to the probe, the determining means connected to the regulating means and the measuring means such that the flow of dilution gas is controlled in response to measured changes in gas density.

3. The system of claim 2, wherein the means for measuring changes in gas density of the sample emission gas comprises:

means for measuring pressure of emission gas in the hollow stack; and means for measuring atmospheric pressure outside the hollow stack, such that the determining means determines the adjusted dilution gas flow value based on the measured change in pressure of the emission gas and the measured change in the atmospheric pressure according to predetermined relationships.

4. The system of claim 2, further comprising:

a means for analyzing one or more constituents of the sample diluted gas, the analyzing means operably connected to the third port of the probe, such that the diluted sample gas is provided to the analyzing means at a controlled dilution ratio.

5. The system of claim 4, further comprising:

a data acquisition system connected to the analyzing means for manipulating gas constituent data determined by the analyzing means.

6. The system of claim 2, wherein the regulating means comprises a transducer for regulating the pressure of the dilution gas and wherein the adjusted dilution gas flow value comprises an adjusted pressure of the dilution gas at the probe.

7. The system of claim 2, wherein the determining means includes a micro-controller.

8. The system of claim 2, wherein the dilution probe further comprises a heater to maintain the probe and all gases contained therein at a controlled temperature.

9. A method for controlling a dilution ratio as measured at a dilution probe connected to a source of dilution gas and to a source of emission gas, the probe combining the dilution gas with a sample of the emission gas to yield diluted sample gas which is emitted from the probe, the dilution ratio defined as the ratio of flow of the diluted sample gas from the probe to flow of the sample emission gas to the probe, the method comprising the steps of:

monitoring gas density of the sample emission gas for an occurrence of a change in the gas density;

upon the occurrence of a change in gas density, determining an adjusted flow value of the dilution gas based on the change in gas density to maintain the constant dilution ratio; and adjusting the flow of the dilution gas to the probe to the determined adjusted dilution gas flow value.

10. The method of claim 9, wherein the flow of dilution gas is adjusted by adjusting the pressure of dilution gas provided to the probe.

11. A method for controlling a dilution ratio for a continuous emission monitoring system, the system comprising a hollow stack emitting an emission gas therein, a dilution gas source operable to provide a flow of dilution gas, a dilution probe extending within the stack for receipt of a sample emission gas, the probe operably connected to the dilution gas source, receiving a flow of sample emission gas, and emitting a diluted sample gas comprising a mixture of dilution gas and sample emission gas, the dilution ratio defined as the ratio of flow of diluted sample gas from the probe to flow of the sample emission gas to the probe, the method comprising the steps of:

measuring changes in gas density of the sample emission gas;

determining an adjusted flow value of the dilution gas based on measured changes in gas density to control the dilution ratio; and adjusting the flow of the dilution gas based on the determined adjusted dilution gas flow value.

12. The method of claim 11, wherein the step of measuring changes in gas density of the sample emission gas comprises:

measuring changes in pressure within the stack;

measuring changes in atmospheric pressure outside the stack; and determining changes in gas density from the measured changes in stack pressure and atmospheric pressure.

* * * * *